Sept. 8, 1953 H. D. DOUGHERTY Plant Pat. 1,216
PEACH TREE
Filed Sept. 4, 1952
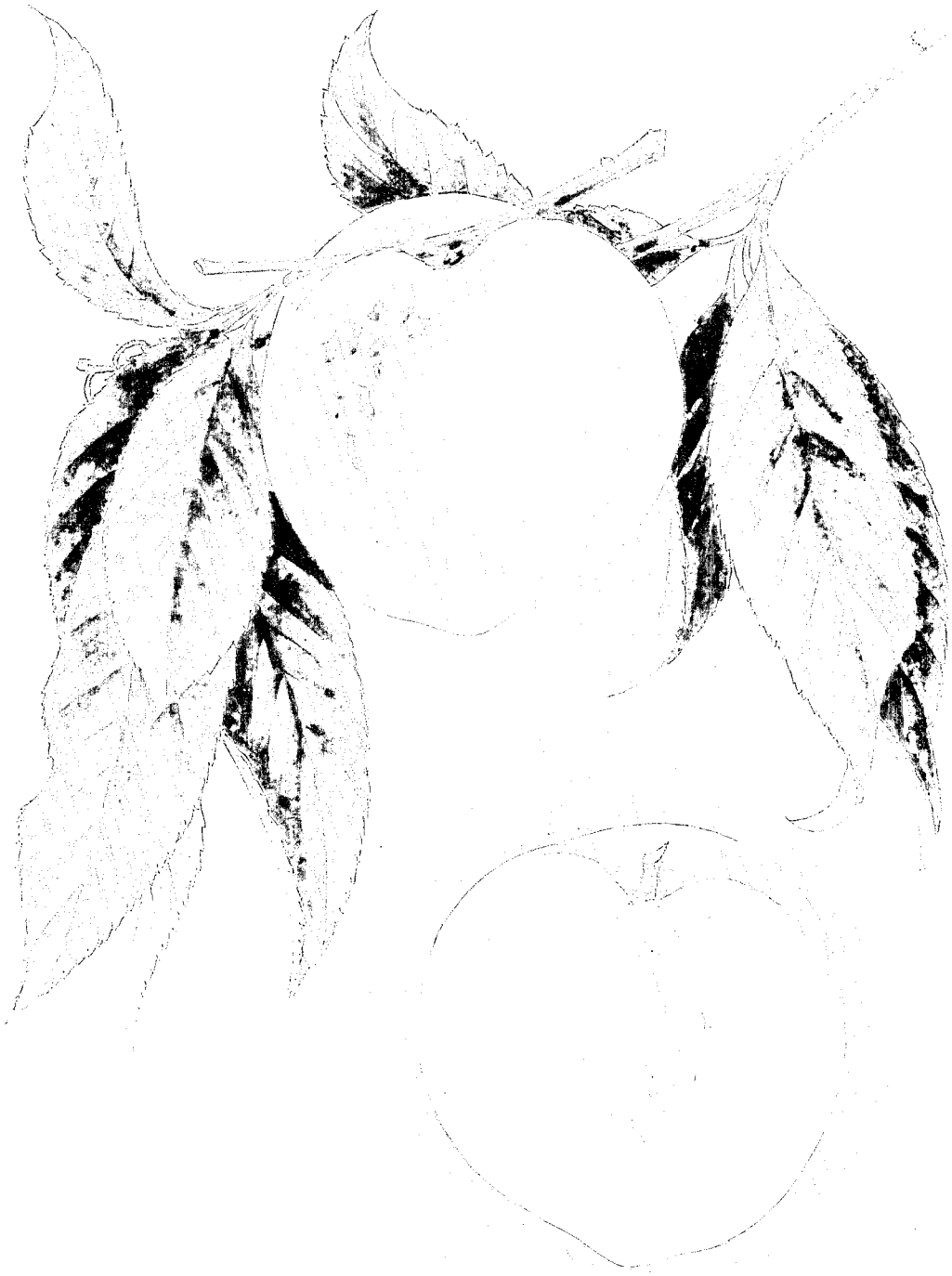
WITNESS
Addison E. Avery
INVENTOR
HAROLD D. DOUGHERTY
Webster & Webster
ATTYS.

Patented Sept. 8, 1953

Plant Pat. 1,216

UNITED STATES PATENT OFFICE 1,216

PEACH TREE

Harold D. Dougherty, Farmersville, Calif.

Application September 4, 1952, Serial No. 307,931

1 Claim. (Cl. 47—62)

The present invention is directed to a new and distinct variety of peach tree which bears yellow-fleshed, semi-freestone fruit. The prime characteristics of such new variety are:

Firstly: An early harvest period as compared to the Triumph peach, which it most closely resembles; and Secondly: Excellent keeping and shipping quality of the fruit.

The firm, yellow-fleshed fruit hangs well on the tree, with a somewhat lengthened ripening period; such fruit being somewhat larger than that of the Triumph peach, and can be picked in a ripened condition, yet remains firm, and does not darken when bruised.

The herein described variety of peach tree was originated by me in the following manner:

Seeds from open-pollenated blossoms of Hale Haven (unpatented) peach trees in an orchard adjacent an orchard of Johnson (unpatented) cling peach trees were taken and planted in nursery rows on my ranch near Farmersville, California. Of a planting of approximately three hundred seeds, some two hundred survived and grew. At the end of the first growing season I selected approximately forty-four seedlings of such two hundred and planted the selected seedlings in tree rows for subsequent observation; the selection having been made on the basis of outstanding vigor, leaf characteristics, and general appearance.

When these forty-four seedlings first fruited, the present variety was selected therefrom, as it was observed that it had a very early ripening date, and was of good eating yet hardy quality.

The fruit was subjected to packing and shipping tests, and its ability to be picked relatively ripe and to then keep and ship well was ascertained.

Subsequently the variety has been successfully asexually reproduced by budding onto mature peach trees of other varieties in an orchard in the Deep Creek District near Farmersville, Tulare County, California; approximately two hundred trees having been budded with this new variety. These reproductions carry forward all of the distinctive characteristics of the parent tree and its fruit.

In the drawings:

Fig. 1 is a perspective view of one of the peaches as attached to a stem with leaves.

Fig. 2 is a sectional view taken axially of the fruit, with the stone exposed.

Referring now more particularly to the pomological details of the new and distinct variety of peach tree, the following is an outline description thereof; all major color plate identifications being by reference to Maerz and Paul Dictionary of Color.

Tree: Large size; vigorous; spreading; medium open; vase formed; hardy; very productive; regular bearer.

Trunk: Stocky; medium texture.

Branches: Stocky; medium texture.

*Color.*—Rusty brown, medium dull.

*Lenticels.*—Medium number; medium size.

Leaves: Average length, 8½″; maximum length, 11″. Average width, 2⅝″; maximum width, 3¾″. Large; oblanceolate; acutely pointed; medium thick as compared with other varieties; medium rugose.

*Color.*—Medium dark as compared with other peach varieties (20–L–7 on top; 20–J–6 on under side).

*Margin.*—Coarsely serrate.

*Petiole.*—Medium length; medium thickness.

*Glands.*—None.

*Stipules.*—Two at base of each leaf stalk.

Flower buds: Hardy; medium size; medium length; conic; free.

Flowers: Average dates first and full bloom—March 2nd and March 5, respectively. Medium late as compared to other varieties of peaches.

*Color.*—Pink.

*Size.*—Large.

Fruit: Maturity when described—ripe, hard (good eating, yet hard enough for very good shipping). Dates of first and last picking—June 5th and 25th, respectively.

*Size.*—Uniform—about 60% large and 40% medium. Average diameter axially—2¾″; average transversely in suture plane—3¾″.

*Form.*—Uniform; oblong.

*Suture.*—Distinct, with slight depression beyond pistil point.

*Ventral surface.*—Rounded slightly.

*Cavity.*—Rounded, with suture showing on one side. Average depth, $1\frac{3}{16}$″; average breadth, $\frac{13}{16}$″. Markings—whitish.

*Base.*—Rounded.

*Apex.*—Moderately prolonged.

*Pistil point.*—Apical.

Skin: Medium thick; tough; tenacious to flesh. Tendency to crack—none, in wet or dry seasons.

*Down.*—Moderate; medium length.

*Color.*—Yellow (9–K–5), with a large portion of the fruit having a red blush (3–J–11, shading to 6–L–6), with some darker mottling (56–L–12).

Flesh:

*Color.*—Yellow (10–L–6 adjacent stone shad- into 11–L–9 toward the outside).

*Surface of pit cavity.*—Whitish.

*Amygdalin.*—Moderate.

*Texture.*—Firm.

*Fibers.*—Few and tender.

*Ripens.*—Evenly.

*Flavor.*—Mild.

*Aroma.*—Distinct.

*Eating quality.*—Fair to good.

Stone: Semi-free.

*Fibers.*—Short; retains short fiber-like threads along ridges.

*Size.*—Medium. Average length, $1\frac{5}{16}''$; average breadth, $\frac{15}{16}''$; average thickness, $\frac{3}{4}''$.

*Form.*—Oblong.

*Base.*—Straight.

*Hilum.*—Oblong.

*Apex.*—Acute.

*Sides.*—Slightly unequal.

*Surface.*—Irregularly furrowed near base.

*Ridges.*—Rounded toward base.

*Pits.*—Elongated.

*Ventral edge.*—Regular, without wing toward base.

*Dorsal edge.*—Narrow, with shallow groove.

*Ridges.*—On either side, interrupted.

*Color.*—Light beige (11–D–6).

*Tendency to split.*—Slight.

Use: General market for fresh eating.

Keeping quality: Very good.

As compared to the Triumph (unpatented) peach, which it most closely resembles, the present variety is substantially distinguishable therefrom in that it has an earlier ripening period of approximately five to ten days when grown under the same soil and climatic conditions. The fruit of the instant variety is somewhat larger, firmer, and keeps and ships better.

Additional distinctions are the absence of glands in the present variety, whereas the Triumph has globose glands, and the marginal structure of the leaves here is serrate, whereas the leaves of the Triumph peach are crenate.

The tree of the present variety is somewhat more vigorous than that of the Triumph peach, with a large blossom as compared to the small blossom of the latter.

The tree and its fruit herein described may vary in slight detail due to climatic and soil conditions under which the variety may be grown.

Having thus described my invention, I claim:

A new and distinct variety of peach tree, substantially as described and illustrated, characterized by yellow-fleshed, semi-freestone fruit having a ripening period averaging five to ten days earlier than the Triumph peach, the fruit hanging well on the tree, with a somewhat lengthened ripening period, remaining firm when picked ripe, having excellent keeping and shipping qualities, and not darkening when bruised; and the tree being further characterized by large size, vigorous growth, leaves having a crenate marginal structure, an absence of glands, and a large blossom.

HAROLD D. DOUGHERTY.

No references cited.